United States Patent [19]

Dam

[11] Patent Number: 4,733,560
[45] Date of Patent: Mar. 29, 1988

[54] LIQUID SENSING SYSTEM

[75] Inventor: Naim Dam, Oakland Gardens, N.Y.

[73] Assignee: Introtek International, Inc., Deer Park, N.Y.

[21] Appl. No.: 898,753

[22] Filed: Aug. 13, 1986

Related U.S. Application Data

[63] Continuation of Ser. No. 544,574, Oct. 24, 1983, abandoned.

[51] Int. Cl.[4] .............................................. G01F 23/22
[52] U.S. Cl. .................................... 73/304 C; 73/313; 324/61 R; 340/620
[58] Field of Search ...................... 73/304 C, 295, 313; 328/4; 331/65; 340/620, 602, 604; 324/61 R

[56] References Cited

U.S. PATENT DOCUMENTS

| | | | |
|---|---|---|---|
| 3,062,994 | 11/1962 | Mesh | 73/304 C X |
| 3,213,438 | 10/1965 | Felice et al. | 73/290 V |
| 3,254,333 | 5/1966 | Baumoel | 73/304 C |
| 3,477,460 | 11/1969 | Dotto | 73/304 R X |
| 3,641,544 | 6/1970 | Radin | 73/304 R |
| 3,878,724 | 4/1975 | Allen | 374/170 X |
| 3,944,994 | 3/1976 | Fanshawe | 331/65 |
| 3,978,352 | 8/1976 | Rose | 328/4 X |
| 4,102,194 | 7/1978 | Eng | 374/170 X |
| 4,110,746 | 8/1978 | Furukawa et al. | 374/170 X |
| 4,244,385 | 1/1981 | Hotine | 73/304 R X |
| 4,262,264 | 4/1981 | Vandegraaf | 331/4 |
| 4,319,484 | 3/1982 | Keller | 73/304 C |
| 4,347,740 | 9/1982 | Townsend | 73/304 C |
| 4,367,462 | 1/1983 | Dressler | 73/304 R |
| 4,382,382 | 5/1983 | Wang | 73/304 R |
| 4,413,810 | 11/1983 | Tenberg et al. | 73/304 R X |
| 4,416,153 | 11/1983 | Williams | 73/295 |
| 4,444,051 | 4/1984 | Yamaki et al. | 73/304 C |
| 4,459,561 | 7/1984 | Clark et al. | 331/65 |
| 4,466,282 | 8/1984 | Kuhnel | 73/304 R |
| 4,471,656 | 9/1984 | Sanders et al. | 73/290 R X |

Primary Examiner—Daniel M. Yasich
Attorney, Agent, or Firm—Darby & Darby

[57] ABSTRACT

A liquid level sensing system having a sensing head with a pair of mutually insulated metal electrodes, one of the electrodes connected to the output of an amplifier and the other to the input. The gain of the amplifier is sufficienty high such that it will oscillate when the electrodes are immersed in a liquid and will be non-oscillatory when the electrodes are in air. The oscillation of the amplifier is detected to produce a signal corresponding to the presence of a liquid and also its characteristic.

7 Claims, 3 Drawing Figures

LIQUID SENSING SYSTEM

This is a continuation-in-part, of application Ser. No. 544,574, filed Oct. 24, 1983 and now abandoned.

The present invention relates to a liquid level sensing system of the contact type. Various types of systems exist, including, for example, those of the ultrasonic type, in which a sensor is placed in the liquid, the capacitive type, conductivity, etc. Each of these types of sensors, as well as others, successfully operates in various applications and, at the same time, also does not function for others.

The present invention is directed to a liquid level sensor which utilizes an impedance, or self-oscillating principle, which has been found to be useful for a variety of applications such as for example, highly aerated liquids and in liquids which have little or no electrical conductivity. In accordance with the invention, the system uses a closed loop oscillator comprising an amplifier whose input and output are each respectively connected to an electrode which respectively functions as receiving and transmitting electrodes which are to be immersed in the liquid. The liquid into which the electrode are immersed is part of the closed loop. If liquid is present between the electrodes, then the amplifier will oscillate and the resulting oscillating waveform can be detected. If there is no liquid, then the circuit does not oscillate. The frequency of oscillation of the circuit is dependent upon the type of liquid into which the electrodes are immersed. Therefore, a liquid identification function also can be performed.

It is therefore an object of the present invention to provide a liquid sensing system.

A further object is to provide a liquid sensing system in which a pair of electrodes are immersed into the liquid and the liquid becomes part of an oscillating circuit.

Another object is to provide a liquid sensing system which operates with a wide variety and types of liquids.

Other objects and advantages of the present invention will become more apparent upon reference to the following specification and annexed drawings in which.

Figure 1:
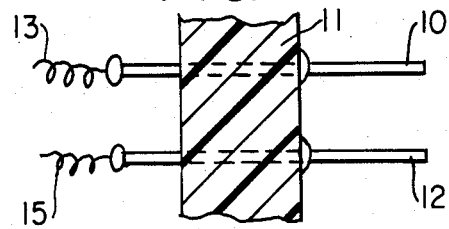
FIG. 1 is a view in section of the sensing head.

Referring to FIG. 1, the sensor head for the system includes a pair of metallic electrodes 10,12, such as wire or pins, of a suitable material, such as stainless steel. Any other suitable metal can be used, depending upon the type of liquid into which the electrodes are to be immersed. The electrodes 10,12 are mounted in an insulating body 11, e.g. of epoxy, plastic, glass or ceramic, or other suitable material so that they do not electrically short circuit. For high pressure applications, separate insulators can be used for each electrode and mounted in a metal body. The body can have threads or other suitable fasteners to mount it in the wall of a pipe, tank or vessel. The particular materials used for the insulator and its carrying body, if any, depend upon the particular application, type of liquid, temperature, pressure, etc.

A lead wire 13,15 is connected to each of its respective electrodes 10,12. The lead wires may be a coaxial cable. The lead wires connect the sensor head to an electric circuit which can be adjacent or remote from the sensor head. Also, the sensor head and the electronic circuit can be housed in the same package.

Figure 2:
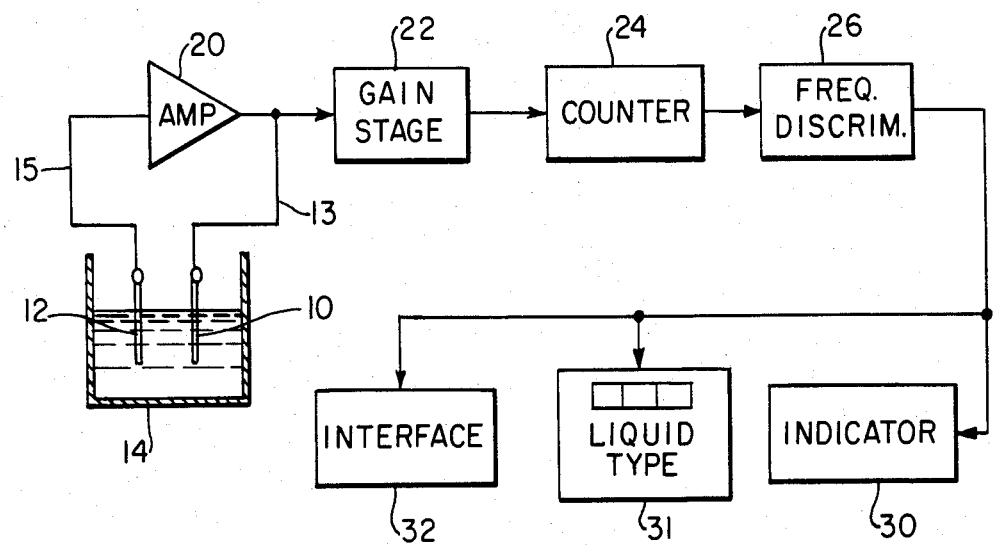
FIG. 2 is a schematic block diagram of the circuit.

FIG. 2 shows the circuit of the invention in schematic block diagram form. The electrodes 10,12 are shown immersed in a liquid in a container 14. As should be apparent, the sensor head of FIG. 1 can be mounted in the wall of any pipe, tank or vessel and at any angle with respect thereto, to serve as a liquid level sensor. Electrode 10, which is the transmitting electrode of the circuit, has its lead 13 connected to the output of an amplifier 20 and electrode 12, which is the receiving electrode of the circuit, has its lead 15 connected to the input of an amplifier 20. Amplifier 20 is any suitable analog amplifier of the medium or high gain type which is commonly available in integrated circuit form, i.e. an IC chip.

The output of amplifier 20 is applied to the input of another amplifier 22, which also is of the analog type. Amplifier 22 is not absolutely necessary but is desirable to provide additional gain and also isolation and buffering.

The output of amplifier 22 is applied to the input of a counter 24. Counter 24 is a conventional circuit and basically serves as a signal processor in that it output squares up the output signals from the amplifier 20, which are generally sinusoidal or alternating in form. For example, for each half cycle of sine wave input, the counter will produce a pulse output. The output frequency of the counter corresponds to the oscillation frequency of the amplifier 20. The counter also can divide the frequency, to produce one output pulse for every predetermined number of input signals, to improve the circuit signal to noise ratio. The counter 24 also can be a digitizer, i.e., a conventional circuit which has a threshold detector and a squaring circuit. However, a counter is more economical and operates satisfactorily in the present circuit.

The output of counter 24 is applied to the input of a frequency discriminator circuit 26. This is also a conventional circuit which produces an output voltage corresponding to the input signal frequency. In the present invention, the type of frequency discriminator used depends upon the use for which the sensing circuit is to be made. If only the presence of liquid is to be sensed, then the discriminator 26 has a wide response curve and produces substantially the same voltage output for the wide range of frequency of input signals. That is, the system is not particularly interested in the frequency of the signal but merely that one is there. In this case, the discriminator output drives an indicator device 30. This can be a relay, alarm, light, etc. A suitable amplifier driver can be used if needed.

If a type of liquid is to be determined, then a precise frequency voltage output response is desired. Here, a precise type frequency discriminator or bank of discriminators responsive to different frequencies can be used. If the discriminator is of the voltage responsive type, then the output voltage will be representative of the type of liquid. This type of output which can be, for example, an analog or digital voltmeter or oscilloscope, as shown by block 31.

To make an interface measurement between two liquids, as shown by block 32 the frequency responsive characteristic of the circuit is also used. For example, for an oil-water interface, the output frequency will be different for the water and for the oil. The change of frequency can be measured, for example, by a voltage output from the discriminator, as the location of the interface shifts relative to the sensor.

Figure 3:
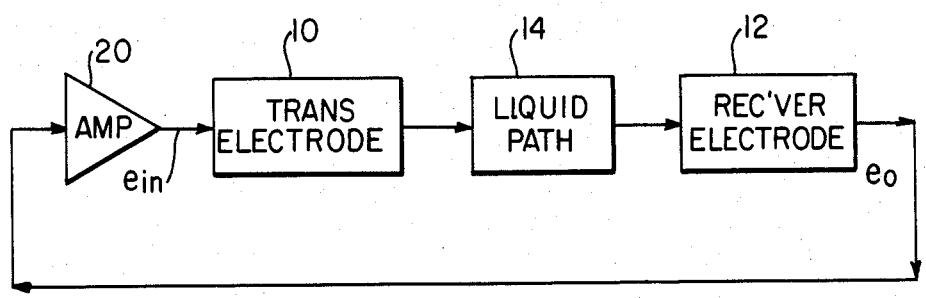
FIG. 3 is a block diagram showing the theory of the oscillator.

Considering now the operation of the circuit, FIG. 3 shows the electrical equivalent circuit. The amplifier 20 has its output connected to the transmitter electrode 10 and its input to the receiver electrode 12 with the liquid path between them. Amplifier 20 produces a voltage $e_{in}$ to the transmitter electrode and receiver electrode 12 a voltage $e_0$ which is applied to the input of the amplifier.

FIG. 3 shows the sensing system as a closed loop in Laplace symbology. In the figure
$\phi_1(s)$ = the gain of the amplifier
$\phi_2(s)$ = the feedback path which includes the electrodes 10,12 and the liquid
$(s)$ = the Laplace operator.
In the circuit of FIG. 3, the closed loop gain G is given by:

$$G = \frac{\phi(s)}{1 + \phi_1(s) \cdot \phi_2(s)}$$

The stability of the closed loop is determined by the nature of the roots of equation.

$$1 + \phi_1(s) \cdot \phi_2(s) = 0$$

Each root of the equation $\theta_1(s) \cdot \theta_2(s) = -1$ defines a solution of $$Ke^{st}$$

where
$s = \sigma + jw$
t = time Three conditions are possible: If
$\sigma = 0$ —oscillations of constant amplitude will be produced.
$\sigma = +$ (positive value) the oscillations increase in amplitude with time.
$\sigma = -$ (negative value) the oscillations decrease in amplitude with time.

From the above analysis, for sustained oscillation to occur, the open loop gain must be unity, and the loop phase shift is an integral number of $2\pi$ radians. The required minimum amplifier gain for a given liquid and a constant path between two sensor electrodes is given by the ratio of the signal applied to the transmitter sensor electrode to the minimum amplitude of the signal induced in the receiver electrode with the given liquid as a feedback path.

When liquid is not present, the air gap between the two electrodes 10, 12 of the sensor head has a very high impedance and there is not enough feedback to cause oscillation. When a liquid is inserted between the two electrodes, the characteristic impedance changes and allows oscillation to occur.

If the type of liquid between the electrodes is changed, the oscillation frequency of the amplifier automatically changes to meet the closed loop criteria for oscillation. Therefore, the oscillation frequency can be detected to determine different liquid characteristics. In other words, the system can be used to determine different types of liquids in terms of the frequency produced by the closed loop oscillator. To accomplish this, for example, the voltage of the discriminator can be used when the discriminator has a frequency vs. voltage characteristic.

It also shall be noted that the frequency output of the oscillator will change if the distance between the electrodes changes.

The present invention provides a novel liquid level device with a cost effective design. It has been found to operate in applications where other devices such as ultrasonic, capacitive or conductivity measuring instruments have failed.

The sensor circuit works in high pressure, high temperature and a highly aerated liquid where ultrasonic and capacitance sensors fail. Also, the system gain is high enough so it works for both conductive as well as non-conductive liquid.

What is claimed is:

1. A system for detecting the presence or absence of a liquid in a volume comprising:
    sensor means having a pair of electrically conductive passive electrodes which are spaced apart by and extend from electrical insulating means for insertion into said volume,
    electronic oscillator means comprising an amplifier in amplifier means having an input and an output, one of said electrodes of said sensor means being electrically coupled to said amplifier input and the other to said amplifier output, said spaced apart electrically conductive electrodes of said sensor means and the space therebetween forming a sole feedback circuit signal path between said output and said input of said amplifier means, said feedback circuit in the absence of a liquid in the space between said two electrodes of said sensor means being open to provide substantially no feedback signal to said amplifier means so that said oscillator means will be non-oscillatory and said feedback circuit being closed to provide a positive feedback signal when liquid is present in said space due to a change in phase of the signal path between said two electrodes to cause said oscillator means to oscillate and thereby indicate the presence of a liquid in the space between said two electrodes; and
    the amplifier is connected to counter means, a frequency discriminator means and indicator means for producing an output control signal.

2. A liquid detection system as in claim 1 further comprising means for producing an output control signal when said amplifier means is oscillating.

3. A liquid detection system as in claim 2, wherein said means for producing said control signal comprises means for measuring the frequency of oscillation of said amplifier means.

4. A liquid detection system as in claim 1, further comprising means for measuring the frequency of oscillation of said amplifier means.

5. A liquid detection system as in claim 2, wherein said means for producing the output control signal comprises counter means responsive to the frequency of oscillation of said amplifier means.

6. A liquid detection system as in claim 5, further comprising means coupled to said counter means for indicating the frequency of oscillation of said amplifier means in response to the count of said counter means.

7. A liquid detection system as in claim 4, wherein said frequency measuring means includes frequency discriminator means for producing an output signal corresponding to the frequency of oscillation of said amplifier means.

* * * * *